(12) United States Patent
Smit

(10) Patent No.: US 8,282,952 B2
(45) Date of Patent: Oct. 9, 2012

(54) INSECT ATTRACTANT

(75) Inventor: Christoffel J. Smit, Citrusdal (ZA)

(73) Assignee: Activetrad (Proprietary) Limited, Citrusdal (ZA)

( * ) Notice: Subject to any disclaimer, the term of this patent is extended or adjusted under 35 U.S.C. 154(b) by 309 days.

(21) Appl. No.: 12/531,245

(22) PCT Filed: Mar. 11, 2008

(86) PCT No.: PCT/IB2008/050874
§ 371 (c)(1),
(2), (4) Date: Nov. 2, 2009

(87) PCT Pub. No.: WO2008/110984
PCT Pub. Date: Sep. 18, 2008

(65) Prior Publication Data
US 2010/0119473 A1  May 13, 2010

(30) Foreign Application Priority Data

Mar. 12, 2007 (ZA) .................................. 2007/02086
May 21, 2007 (ZA) .................................. 2007/04073
Oct. 1, 2007 (ZA) .................................. 2007/08349

(51) Int. Cl.
*A01N 25/34* (2006.01)

(52) U.S. Cl. ........ 424/409; 424/405; 424/406; 514/284; 514/439; 514/561; 514/562; 514/563; 514/564; 514/565; 514/566; 514/642; 514/669; 514/727

(58) Field of Classification Search .................... None
See application file for complete search history.

(56) References Cited

U.S. PATENT DOCUMENTS

2005/0165070 A1 * 7/2005 Bonfiglioli et al. ........... 514/365
2005/0181001 A1 8/2005 Roentsch et al.

FOREIGN PATENT DOCUMENTS

WO WO-2006/045122 A2 4/2006
WO WO-2008/012756 A2 1/2008

OTHER PUBLICATIONS

Sirugue D, et al, "2-Methylthiazolidine and 4-Ethylguaiacol, Male Sex-Pheromone Components of the Cockroach Nauphoeta-Cinerea (Dictyoptera Blaberidae)-A Reinvestigation" Journal of Chemical Ecology, Plenum Publishing Corporation, US, vol. 18, No. 12, Jan. 1, 1992, p. 2261-2276, XP009103412, ISSN: 0098-0331.

Tong H.C. et al: Topical Mosquito Repellents VIII: Substituted 2-Thio-4-Thiazolidinones and 2, 4-Thiazolidinediones Mosquito News, vol. 35, No. 1, Mar. 1975 pp. 76-82, XP009103981 CA, USA.

* cited by examiner

*Primary Examiner* — Neil Levy

(74) *Attorney, Agent, or Firm* — Connolly Bove Lodge & Hutz LLP

(57) ABSTRACT

The invention relates to insect attractants containing compounds with pentagonal heterocyclic structures that are effective in attracting fruitflies.

18 Claims, No Drawings

INSECT ATTRACTANT

CROSS REFERENCE TO RELATED APPLICATIONS

This application is a national stage application (under 35 U.S.C. §371) of PCT/IB2008/050874, filed Mar. 11, 2008 which claims benefit of South African applications 2007/02086 filed Mar. 12, 2007, 2007/04073, filed May 21, 2007 and 2007/08349, filed Oct. 1, 2007.

FIELD OF THE INVENTION

THIS INVENTION relates to attractants for insects that can be used in pest control.

BACKGROUND TO THE INVENTION

A number of chemical compounds have been identified that attract some insects and/or other pests under some conditions and these attractant compositions are used in pest control to lure insects toward pest control means such as traps and toxins. However, many of these attractants are not sufficiently effective in attracting the species that are being targeted, are harmful to the environment, are too costly, etc.

The present invention seeks to provide attractants that are effective in attracting insects.

SUMMARY OF THE INVENTION

According to a first aspect of the present invention, there is provided the use of a compound to attract insects, said compound including a pentagonal heterocyclic structure.

The compound may be a variant of thiazole and may have any degree of ring saturation to include thiazoles, thiazolines and thiazolidines. The S— and N— atoms may be placed in various positions in the heterocyclic structure, e.g. in the 1,2 (=iso) position or in the 1,3 position. The compound may include functional attachments such as N-acyl and 4-carboxylic acid, i.e. the compound may be N-acetyl thiazolidine carboxylic acid (NATC).

The compound may be a variant of oxazole and may have any degree of ring saturation to include oxazoles, oxazolines and oxazolidines. The O— and N— atoms may be placed in various positions in the heterocyclic structure, e.g. in the 1,2 (=iso) position or in the 1,3 position.

The compound may be a variant of furan and may have any degree of ring saturation to include di-hydro- and tetrahydrofurans.

The compound may be a variant of thiophene and may have any degree of ring saturation to include di-hydro- and tetrahydro-thiopenes.

The compound may be a variant of pyrrole and may have any degree of ring saturation to include pyrroles, pyrrolines and pyrrolidines.

The compound may include any functional attachments such as N-acyl, 4-carboxylic acid, and/or metal salts and/or ammonium- and organic amine salts of the carboxylic acid.

According to another aspect of the present invention, there is provided a pest control composition, said composition including at least one variant of a compound as described hereinabove, which may serve as an attractant for insects.

The composition may include additives, especially additives that act synergistically in attracting insects, such as any amino acid (including amino acids from hydrolized proteins), baits such as molasses, bait toxins (poisons) such as Malathion, or the like.

In particular, the composition may include a tertiary or quaternary amine such as Trimethylamine, but more preferably Tri-ethanolamine (TEA), Choline chloride or Acetyl choline chloride (AChCl) and/or may include Ammonium acetate (NH4Ac). Instead or in addition, the composition may include Trimethylamine (TMA) and/or acetic acid (HAc). The organic amines may include gamma amino butyric acid, ethyl 4-aminobutyrate, tryptamine and/or Octopamine, all of which are also connected to neurotransmitters.

The composition may include an acetamide such as N-Methylacetamide, N-Ethyl acetamide, N-Ethyl pentanamide, N-Ethyl N-methyl formamide, or a short chain thio amide.

The use of a compound or composition as described hereinabove may further be enhanced by using it in combination with light sources, such as light signals powered from photovoltaic cells.

EXAMPLES

For a better understanding of the present invention, and to show how it may be carried into effect, a number of non-limiting, illustrative experimental examples are described.

Background

The original aim of these experiments was to identify cheaper but still effective fruitfly attractants comparable to an insect attractant that is commercially available in South Africa under the trade name "Hymlure"; especially in catching female fruitflies. Ginger oil was identified to be very effective in catching medfly (Mediterranean fruitfly or *Ceratitis capitata*) females but not male medflies and pumpkinflies. It was also too expensive to compete with Hymlure. Various good male medfly catching attractants were identified. In the subsequent further search for alternative cheaper but still effective fruitfly attractants, the attractants of the present invention had been identified as being very highly attractive towards both male and female medflies. It also attracts pumpkinflies (*Dacus cucurbitae*) at about the same degree as Hymlure or other commercially available attractants such as GF-120. The example of the composition of the present invention that was used in these experiments is N-acetyl thiazolidine carboxylic acid (NATC).

In Experiments 1 to 13, it was assumed that NATC was the only ingredient in Yield Plus (YP), a commercial plant growth stimulant, that would be effective in attracting insects and the experiments were conducted using NATC as included in YP, i.e. that practically all the attractive strength of YP towards insects was the result of its NATC content.

Subsequently, further experiments were conducted to identify combinations of ingredients for a composition in accordance with the present invention for a medfly attractant that would be particularly effective in attracting female medflies. In these experiments NATC was used in pure form (referred to as "NATC") and was used as included in YP (referred to as "YP-B").

Experimental Procedure (Experiments 1 to 13, 23 and 24)

Maggots of single sex medflies were obtained from a medfly breeding station at Infruitec, Stellenbosch, South Africa and were kept in a moist hatching box at room temperature. After about one week the first maggots started to hatch and these maggots were measured out at one tablespoon per paper bag, which was then subsequently sealed with staples and left to hatch further in the paper bags for one to two days. These paper bags with hatched medflies were then attached by means of a staple gun underneath the bottom of a standard yellow coloured attractant-loaded Delta trap. These traps are the same as those used for monitoring pest insect populations by using sex pheromones inside it as attractants. The traps with their sticky pads were obtained from the Chempack Company in Paarl, South Africa. After about one week, the medfly catches were counted and recorded. In the case of single traps, they were hung in trees at about 10 m×10 m spacing. In the case of the paired traps, two traps were hung adjacent each other in the same tree with their open sides side-by-side so that the fruitflies had to make a choice between attractants. The experiments targeting pumpkinflies were conducted on naturally occurring populations and with the same configurations of single and paired traps.

The compositions which are commercially available in South Africa and to which reference is made in the descriptions of experimental results are:

| | |
|---|---|
| GF-120 | insect attractant |
| Hymlure | insect attractant |
| Pyrethrum | poison |
| Exterminator | poison |
| Suntap | poison |
| Rotenone | poison |
| Kingbo | poison |
| Bioneem | poison |
| Malathion | poison |
| Yield Plus (YP) | plant growth stimulant |

Where relevant, the concentrations of compositions are indicated as a suffix.

Experimental Procedure (Experiments 14 to 22)

Delta traps with sticky pads loaded with the indicated odorant substances, were hung up inside a fluorescent light illuminated, ventilated, air-conditioned, temperature controlled room (28 degrees Celsius). Room size is 6 m×3.0 m×2.5 m. Female medflies were released inside this room in mean quantities of about 500 available per trap. Trap catches were counted one day after release.

Results

Experiment 1 (23 Mar. 2007 to 30 Mar. 2007)

Female medflies in citrus orchard
Delta trap catches with different attractants: Single traps

| Attractants: undiluted | Rep. 1 | Rep. 2 | Rep. 3 | Rep. 4 | Rep. 5 | Mean |
|---|---|---|---|---|---|---|
| GF-120 | 15 | 20 | 19 | 8 | 12 | 14.8 |
| Hymlure | 22 | 13 | 25 | 12 | — | 18.0 |
| Ginger oil 0.1% + Caryophyllene 0.1% + Terpinyl acetate 0.1% + Molasses 3% | 12 | 10 | 20 | 11 | 18 | 14.2 |
| NATC - 5% in YP | 240 | 80 | 110 | 112 | 124 | 133.2 |

Findings:
Using single traps, NATC 5% in YP attracted between 7.4 and 9.5 times as many female medflies as the other attractants in undiluted form.

Experiment 2 (12 Apr. 2007 to 16 Apr. 2007)

Female medflies in peach orchard
Delta trap catches with different attractants: Paired traps

| Attractant | Rep. 1 | Rep. 2 | Rep. 3 | Mean |
|---|---|---|---|---|
| NATC - 5% in YP | 36 | 76 | 57 | 56.3 |
| GF-120 undiluted | 10 | 40 | 23 | 24.3 |
| NATC - 1% in YP | 34 | 43 | 73 | 50.0 |
| GF-120-undiluted | 14 | 10 | 25 | 16.3 |

Findings:
Using paired traps:
NATC 5% in YP attracted 2.3 times as many female medflies as undiluted GF-120.
NATC 1% in YP attracted 3.1 times as many female medflies as undiluted GF-120.

Experiment 3 (12 Apr. 2007 to 16 Apr. 2007)

Female medflies in peach orchard
Delta trap catches with different attractants: Single traps

| Attractants | Rep. 1 | Rep. 2 | Rep. 3 | Rep. 4 | Rep. 5 | Mean |
|---|---|---|---|---|---|---|
| GF-120 undiluted | 33 | 30 | 21 | 22 | 37 | 28.6 |
| NATC - 5% in YP | 80 | 56 | 35 | 77 | 45 | 58.6 |

Findings:
Using single traps, NATC 5% in YP attracted 2.1 times as many female medflies as undiluted GF-120.

Experiment 4 (12 Apr. 2007 to 16 Apr. 2007)

Male medflies in peach orchard
Delta trap catches with different attractants: Paired traps

| Attractants | Rep. 1 | Rep. 2 | Rep. 3 | Rep. 4 | Rep. 5 | Mean |
|---|---|---|---|---|---|---|
| GF-120 undiluted | 16 | 27 | 49 | 55 | 64 | 42.2 |
| NATC - 5% in YP | 80 | 101 | 91 | 114 | 78 | 92.8 |

Findings:
Using paired traps, NATC 5% in YP attracted 2.2 times as many male medflies as undiluted GF-120.

Experiment 5 (23 Apr. 2007 to 7 May 2007)

Female medflies in peach orchard
Delta trap catches with different attractants: Paired traps

| Attractants | Rep. 1 | Rep. 2 | Rep. 3 | Rep. 4 | Rep. 5 | Mean |
|---|---|---|---|---|---|---|
| GF - 120-5% | 38 | 55 | 80 | 73 | 71 | 63.4 |
| NATC - 5% in YP | 188 | 208 | 372 | 384 | 338 | 298.0 |

Findings:

Using paired traps over 14 days NATC 5% in YP attracted 4.7 times as many female medflies as GF-120 5%.

Experiment 6 (12 Apr. 2007 to 16 Apr. 2007)

Female medflies in peach orchard
Delta trap catches with different attractants: Paired traps

| Attractants | Rep. 1 | Rep. 2 | Rep. 3 | Rep. 4 | Rep. 5 | Mean |
|---|---|---|---|---|---|---|
| GF - 120-5% | 81 | 64 | 37 | 67 | 58 | 61.4 |
| NATC - 1% in YP | 225 | 138 | 144 | 128 | 190 | 165.0 |

Findings:

Using paired traps over 14 days NATC 1% in YP attracted 2.7 times as many female medflies as GF-120 5%

Experiment 7 (26 Apr. 2007 to 1 May 2007)

Female medflies; interaction of NATC 1% in YP with various bait poisons in citrus orchards; means of three replications with paired traps (NATC 1% in YP alone vs NATC 1% in YP plus 0.5% poison)

| | Bait poisons | | | | | |
|---|---|---|---|---|---|---|
| Attractant | Pyrethrum | Exterminator | Suntap | Rotenone | Kingbo | Bioneem |
| NATC 1% in YP | 75.5 | 80.0 | 116.0 | 86.3 | 54.0 | 89.0 |
| NATC 1% in YP + Poison | 19.0 | 40.3 | 80.3 | 96.3 | 58.0 | 132.0 |

Findings:

The experimental results indicate that when bait poisons in the forms of Pyrethrum, Exterminator and Suntap were combined with NATC in YP, female medfly trap catches were suppressed. With Rotenone and Kingbo there are small differences in attraction between traps with and without poison while with Bioneem nearly 1.5 times more female medflies were caught with poison than without it.

Experiment 8 (10 May 2007 to 11 May 2007)

Mixed gender medflies; interaction of NATC 1% in YP with various bait poisons in citrus orchards; means of three replications with paired traps (NATC 1% in YP alone vs NATC 1% in YP plus 0.5% poison)

| Attractant | Rep. 1 | Rep. 2 | Rep. 3 | Mean |
|---|---|---|---|---|
| NATC 1% in YP | 23 | 60 | 45 | 42.7 |
| NATC 1% in YP + Kingbo 0.5% | 53 | 73 | 95 | 73.7 |
| NATC 1% in YP | 35 | 26 | 26 | 29.0 |
| NATC 1% in YP + Bioneem 0.5% | 45 | 36 | 55 | 45.3 |

Findings:

With bait poison in the form of Kingbo, nearly 1.7 times more female medflies were caught with poison than without it while with poison in the form of Bioneem nearly 1.6 times more female medflies were caught with poison than without it.

Experiment 9 (23 Apr. 2007 to 07 May 2007)

Female medflies; interaction of NATC 1% with various bait/poison components in peach orchard: Paired traps

| Attractant | Rep. 1 | Rep. 2 | Rep. 3 | Rep. 4 | Mean |
|---|---|---|---|---|---|
| NATC 1% in YP | 73 | 112 | 26 | 74 | 71.3 |
| NATC 1% in YP + Malathion 0.2% | 70 | 170 | 77 | 101 | 104.5 |
| NATC 1% in YP | 59 | 70 | 68 | 44 | 60.3 |
| NATC 1% in YP + Molasses 3% | 58 | 72 | 71 | 53 | 63.5 |
| NATC 1% in YP | 71 | 70 | 54 | 110 | 76.3 |
| NATC 1% in YP + Malathion 0.2% + Molasses 3% | 68 | 69 | 82 | 97 | 79.0 |

Findings:

In combination with NATC 1% in YP, Malathion 0.2% caught nearly 1.5 times more female medflies with poison than without it, while with Molasses or with a combination of Molasses and Malathion there were little differences. It thus seems to be safe to use these ingredients together in poisoned baits.

Experiment 10 (20 Dec. 2006 to 27 Dec. 2006)

Pumpkinflies (*Dacus cucurbitae*)—natural populations of mixed sexes in muskmelon fields
Delta trap catches with different attractants: Single traps

| Attractants | Rep. 1 | Rep. 2 | Mean |
|---|---|---|---|
| GF-120 undiluted | 16 | 14 | 15.0 |
| Hymlure | 36 | 19 | 27.5 |
| NATC- 5% in YP | 22 | 25 | 23.5 |

Findings:

With pumpkinflies, there are no big differences between the attractivity of GF-120 undiluted, Hymlure and NATC 5% in YP, contrary to what happened in the experiments on medflies.

Experiment 11 (8 Jan. 2007 to 22 Jan. 2007)

Pumpkinflies—natural populations of mixed sexes in muskmelon fields
Delta trap catches with different attractants: Single traps

| Attractants | Rep. 1 | Rep. 2 | Rep. 3 | Rep. 4 | Mean |
|---|---|---|---|---|---|
| GF-120 undiluted | 3 | 5 | 9 | 4 | 5.3 |
| NATC- 5% in YP | 6 | 8 | 6 | 3 | 5.8 |

Findings:

In this experiment with pumpkinflies, there are no big differences between the attractivity of GF-120 undiluted and NATC 5% in YP.

Experiment 12 (26 Feb. 2007 to 1 Mar. 2007)

Pumpkinflies—natural populations of mixed sexes in muskmelon fields
Delta trap catches with different attractants: Single traps

| Attractants | Rep. 1 | Rep. 2 | Mean |
|---|---|---|---|
| GF-120 undiluted | 19 | 17 | 18 |
| Hymlure | 14 | 11 | 12.5 |
| NATC- 5% in YP | 50 | 15 | 32.5 |

Findings:
In this experiment, it seems as if NATC 5% in YP attracted pumpkinflies somewhat stronger than Hymlure and GF-120.

Experiment 13 (5 Mar. 2007 to 12 Mar. 2007)

Pumpkinflies—natural populations of mixed sexes in muskmelon fields
Delta trap catches with different attractants: Single traps

| Attractants | Rep. 1 | Rep. 2 | Rep. 3 | Rep. 4 | Mean |
|---|---|---|---|---|---|
| GF-120 undiluted | 5 | 5 | 6 | 5 | 5.2 |
| Hymlure | 8 | 6 | 6 | 8 | 7.0 |
| NATC- 5% in YP | 9 | 6 | 28 | 12 | 13.8 |

Findings:
In this experiment, again it seems as if NATC 5% in YP attracted pumpkinflies somewhat stronger than Hymlure and GF-120.

Experiments 1 to 13 have been conducted to assess the efficacy of attractants containing NATC, but the inventor believes that other variants of active compounds including pentagonal heterocyclic structures as mentioned above, will also be effective as an insect attractant. Further, by varying the atoms and their positions in the heterocyclic structure, as well as the functional groups and their positions, the compounds are likely to have different attractive properties to be used to target different insect species and/or sexes.

Experiment 14

| Attractants | Trap catches better than blank control (Means of 2 replications) |
|---|---|
| GF-120-5% | 75.0 |
| Yield Plus-5x diluted (=YP-B 1%) | 70.0 |
| NATC-2.5% + TEA-2.5% | 68.0 |
| NATC-1.7% + TEA-1.7% + HAc-1.7% | 20.0 |
| NATC-1.7% + TMA-1.7% + HAc-1.7% | 35.0 |
| NATC-2.5% + TMA-2.5% | 18.0 |

Findings:
1. GF-120-5%, YP-B-1% and NATC-5%+TEA-5% attracted approximately the same number of female medflies.
2. Addition of acetic acid seems to decrease medfly trap catches with TEA.
3. NATC-2.5%+TEA-2.5% is a much stronger attractant than NATC-2.5%+TMA-2.5%. TEA is also much safer/less toxic than TMA. Thus TEA is a much better choice than TMA in medfly attractants.

Experiment 15

| Attractants | Trap catches better than blank control (Means of 2 replications) |
|---|---|
| NATC-0.5% + TEA-0.5% + NH4Ac 0.5% | 248 |
| NATC-0.5% + TEA-0.5% + Maltol 0.5% | 206 |
| NATC-0.5% + TEA-0.5% | 91 |
| NATC 1% | 177 |

Findings:
NH4Ac-0.5% (Ammonium acetate) is a stronger attracting partner for the NATC-0.5%+TEA-0.5% combination than Maltol 0.5%

Experiment 16

| Attractants | Trap catches better than blank control (Means of 3 replications) |
|---|---|
| NATC-1% + TEA-1% + NH4Ac 1% | 158.0 |
| NATC-1% + TEA-1% + NH4Ac 1% + Molasses 3% | 378.0 |
| Yield Plus 5x diluted (=YP-B-1%) | 245.5 |
| NATC-5% | 227.0 |
| GF-120 5% | 151.5 |

Findings:
(a) In Experiment 13, the addition of NH4Ac 1% to the NATC-1%+TEA-1% mixture increased trap catches of the latter with 272.5%. In this experiment, the further addition of Molasses-3% to the NATC-1%+TEA-1%+NH4Ac 1% mixture, resulted in a further increase of 239% in trap catches.
(b) Trap catches of the mixture NATC-1%+TEA-1%+ NH4Ac 1% were approximately similar to that of GF-120-5%.
(C) Trap catches of pure NATC-5% were near to that of NATC-1% mixed into the Yield Plus formulation indicating the other NATC-synergists present in Yield Plus.

Experiment 17

| Attractants | Trap catches better than blank control (Means of 3 replications) |
|---|---|
| NATC-1% + TEA-1% + NH4Ac 1% + Molasses 3% | 672.5 |
| NATC-0.5% + TEA-0.5% + NH4Ac 0.5% + Molasses 3% | 331.7 |
| NATC-0.5% + TEA-0.5% + NH4Ac 0.5% + Maltol 0.25% + Molasses 3% | 281.7 |
| Yield Plus 5x diluted (=YP-B-1%) | 280.0 |
| GF-120 5% | 274.3 |

-continued

| Attractants | Trap catches better than blank control (Means of 3 replications) |
|---|---|
| NATC 1% | 195.7 |
| TEA-1% + NH4Ac 1% | 68.0 |

Findings:
(a) Trap catches with NATC+TEA-+NH4Ac at 1% each and 0.5% each—both combined with Molasses 3%—were respectively 245.2% and 120.9% higher than that of GF-120 5%.
(b) Trap catches of NATC 1% incorporated into Yield Plus—with a 5× dilution (=YP-B-1%) were 143% better than that of pure NATC 1% and nearly similar to that of GF-120 5%. This again indicates the presence of NATC synergists in Yield Plus.

Experiment 18

| Attractants | Trap catches better than blank control (Means of 2 replications) |
|---|---|
| NATC-1% + TEA-1% + NH4Ac 1% | 304.5 |
| NATC-0.5% + TEA-0.5% + NH4Ac 0.5% | 281.5 |
| NATC-5% | 280 |
| NATC-1% | 150.5 |
| NATC 1% + TEA 1% | 30.0 |
| NATC 1% + TEA 1% + Maltol 0.5% | 124.0 |
| NATC-1% + TEA-1% + NH4Ac 1% | 304.5 |
| NATC-1% + TEA-1% + Ethyl hexanoate 0.1% | 16.0 |
| NATC 1% + Maltol 0.5% | 100.0 |

Findings:
(a) Similar to results of Experiment 12, NH4Ac-0.5% (Ammonium acetate) is a much stronger attracting partner/synergist for the NATC-0.5%+TEA-0.5% combination than Maltol 0.5%
(b) Even the half strength (0.5%) of the NATC+TEA+NH4Ac mixture still attracted only to a small degree less medflies than the full strength (0.1%). Trap catches of the mixture NATC-0.5%+TEA-0.5%+NH4Ac 0.5% were nearly similar to that of NATC-5%.
(c) The interactions between the NATC 1%+TEA 1% mixture and various third partners varied between nearly 50% lower to 10 times higher.

Experiment 19 (High Medfly Population)

| Attractants | Trap catches better than blank control (Means of 3 replications) |
|---|---|
| NATC-1% + AChCl-1% + NH4Ac 1% + Molasse 3% | 745.3 |
| NATC-0.5% + AChCl-0.5% + NH4Ac 0.5% + Molasse 3% | 697.7 |
| Yield Plus 5x diluted (=YP-B1%) | 369.3 |
| NATC-1% + TEA-1% + NH4Ac 1% + Molasse 3% | 248.0 |
| GF-120-5% | 291.0 |

Findings:
(a) The substitution of TEA with AChCl in the 1% NATC/NH4Ac mixtures+3% molasses increased the Trap catches with 300.5% relative to the 1%-NATC/TEA/NH4Ac/3%-Molasses mixture and 256.1% relative to GF120-5%.
(b) The substitution of TEA with AChCl in the 0.5% NATC/NH4Ac mixtures+3% molasses increased the Trap catches with 281.3% relative to the 1%-NATC/TEA/NH4Ac/3%-Molasses mixture and 239.8% relative to GF120-5%.
(c) The 5× diluted Yield Plus (=YP-B 1%) caught 1.269 times the number of female medflies than GF120 5%.

Experiment 20 (Low Medfly Population)

| Attractants | Trap catches better than blank control (Means of 4 replications) |
|---|---|
| NATC-1% + AChCl-1% + NH4Ac 1% + Molasses 3% | 306.3 |
| NATC-0.5% + AChCl-0.5% + NH4Ac 0.5% + Molasses 3% | 211.2 |
| NATC-0.125% + AChCl-0.125% + NH4Ac 0.125% + Molasses 3% | 134.9 |
| NATC-0.0625% + AChCl-0.0625% + NH4Ac 0.0625% + Molasses 3% | 38.5 |
| GF-120 5% | 80.7 |

Findings:
(a) This experiment was done under relatively low medfly population densities. The purpose was to determine the rate of decrease of medfly Trap catches with decreasing concentrations of NATC/AChCl/NH4Ac in order to identify concentrations of the latter mixture in combination with Molasses 3% which caught about double the number of medflies than GF120 5%.
(b) It appears that this may probably be achieved with a concentration of NATC/AChCl/NH4Ac somewhere between 0.125% and 0.5%; maybe about 0.25%. This will be determined in a forthcoming experiment.
(c) A concentration of 1% of the NATC/AChCl/NH4Ac mixture in combination with Molasses 3% attracted 379.6% times the medflies relative to that caught by GF120-5%.
(d) A concentration of 0.0625% of the NATC/AChCl/NH4Ac mixture in combination with Molasses 3% was too low; being about half of the attraction of GF120-5%.

Experiment 21

Lowest effective concentrations and attractiveness of choline chloride vs acetyl choline chloride in comparable mixtures.

| Attractants | Trap catches better than blank control Means - 2 replications |
|---|---|
| NATC-0.5% + Ach Cl-0.5% + NH4Ac 0.5% + 3% molasses | 589.7 |
| NATC-0.25% + Ach Cl-0.25% + NH4Ac 0.25% + 3% molasses | 317.5 |
| NATC-0.125% + Ach Cl-0.125% + NH4Ac 0.125% + 3% molasses | 41.5 |
| NATC-0.0625% + Ach Cl-0.0625% + NH4Ac 0.0625% + 3% molasses | 0 |
| GF-120-5% | 148.7 |

| Attractants | Trap catches better than blank control Means - 2 replications |
|---|---|
| NATC-0.5% + Choline chloride-0.5% + NH4Ac 0.5% + 3% molasses | 305.5 |

Findings:
It appears that the concentration of the NATC/AchCl/ NH4Ac mixture in a 1:1:1 ratio, should not be less that 0.25%, in order to achieve an attractiveness of at least twice that of GF-120,
In the same concentration (i.e. 0.5%) of the above mixture, Acetyl choline chloride (AchCl) attracted 284.2 or 93% more medflies than Choline chloride.
If a commercial formulation were to contain Choline Chloride and acetic acid (which is a fairly important ingredient of Yield Plus), these ingredients may react in this formulation to form acetyl choline chloride.

Experiment 22

Female medfly attraction of NATC-1% used in combination with various other odorants

| Attractants | Trap catches relative to that of NATC-1% Means - 2 replications |
|---|---|
| NATC-1% | 0 (100%) |
| NATC-1% + Gamma amino butyric acid (GABA) (conc*) | +549.0 (370.2%) |
| NATC-1% + Octopamine (conc*) | +285.5 (240.5%) |
| NATC-1% + Ethyl 4-aminobutyrate (conc*) | +222.5 (209.5%) |
| NATC 1% + Tryptamine (conc*) | +208.7 (202.5%) |
| NATC-1% + Acetyl choline chloride-5% | +109.0 (153.7%) |
| NATC-1% + NH4Ac 5% | +40.7 (119.9) |
| NATC-1% + Gramine (conc*) | −58.3 (71.3%) |
| NATC-1% + 3-Methoxy benzamide (conc*) | −106.3 (47.7%) |
| NATC-1% + 2,3,5-trimethyl pyrazine (conc*) | −164.8 (18.9%) |

*Conc = Concentrated, i.e. powder adhered in water suspension, to paper squares

Findings:
Additions to NATC 1% of Gamma amino butyric acid (GABA) with a 370.2% increase relative to that of NATC 1% alone gave the strongest attraction, followed by Octopamine (240.5%), Ethyl 4-aminobutyrate(related to GABA) with 222.5%, Tryptamine (202.5%), Acetyl choline chloride (109.0), and Ammonium acetate (40.7). Gramine, 3-Methoxy benzamide and 2,3,5-Trimethyl pyrazine—in increasing order suppressed medfly attraction.

Experiment 23 (13 Sep. 2007)

Conducted in cool conditions in open air in an orchard, with ambient temperatures ranging between 10 and 22 degrees celcius.

| Test attractants | Female medfly trap catches (4 reps.) |
|---|---|
| NATC 0.5% in Yield Plus (YP-B) [=YP-B 0.5%] | 84 |
| NATC 0.5% alone | 6 |
| NATC 0.5% + Ch Cl 0.5% | 22 |
| NATC 0.5% + A Ch Cl 0.5% | 16 |
| NATC 0.5% + TEA 0.5% | 11 |
| GF120-5% sol. | 14 |

Findings:
Attractiveness under these cool season orchard conditions were all in the range between 14 and 22 female medflies for GF120-5%, NATC 0.5%+A Ch Cl 0.5% and NATC 0.5%+Ch Cl 0.5% which was about 4 times lower than that of a 10 times diluted Yield Plus.

Experiment 24 (17 Sep. 2007)

Conducted in cool orchard conditions similar to those of Experiment 23

| Test attractants | Female medfly trapcatches (4 reps) |
|---|---|
| GF120-5% solution | 16 |
| 1% NATC alone | 5 |
| 0.5% NATC in Yield Plus (YP-B) [=YP-B 0.5%] | 115 |

Findings
The 10 times diluted Yield Plus attracted 7.2 times more female medflies under these cool season orchard conditions than GF 120 5%.
The inventor expects that the attractiveness of NATC+ Cholines or Tri-ethanolamine (TEA) mixtures will compare more favourably to that of GF120 in higher ambient temperatures, based on the results of Experiments 14 to 22, which were conducted at constant temperatures of about 28 to 30 degrees Celsius.
Experiments 12 to 24 have been conducted to assess the efficacy of different combinations of ingredients in attractant compositions according to the present invention.
Tri-ethanolamine:
Tri-etanolamine is a safer and more attractive choice of tertiary or quarternary amine than Trimethylamine. Further, the experimental results indicate that Tri-ethanolamine as a choice of quaternary amine in the NATC/tertiary or quarternary amine/NH4Ac/Molasses mixture can give female medfly attractions comparable to 20% better than GF120—5% at concentrations of 0.5% of the NATC/tertiary or quarternary amine(triethanol-amine)/NH4Ac component.
Acetyl choline chloride:
Acetyl choline chloride as a choice of quaternary amine in the NATC/tertiary or quarternary amine/NH4Ac/Molasses mixture instead of Tri-etanolamine is of similar or better safety and about 3 times more attractive than the tri-ethanolamine mixtures. Comparable attractions of the Acetylcholine chloride substituted mixture with GF120-5% would probably lay at a concentration strength of near 0.1% of the NATC/Quarternary amine/NH4Ac components—in combination with 3% molasses.
The substitution of Acetyl choline chloride instead of tri-ethanolamine as a choice of quaternary amine in the NATC/ tertiary or quarternary amine/NH4Ac/Molasses mixture increased the attraction strength with between 281.3% and 300.5% for similar concentrations of active ingredients.

If double the attractive strength of GF120-5% is set as a target, the experimental results indicated that concentrations of the NATC/AChCl/NH4Ac components in combination with Molasses 3% is approximately between 0.125% and 0.5%; possibly about 0.25%.

The invention claimed is:

1. A method for attracting insects to a trap or toxin which comprises providing a composition comprising N-acetyl thiazolidine carboxylic acid (NATC) and at least one member selected from the group consisting of ammonium acetate; a quaternary amine; a tertiary amine; a primary amine; and an amino acid; in the vicinity of said trap or toxin and wherein said insects are of the species *Ceratitis capitata* or of the species *Dacus cucurbitae*.

2. The method according to claim 1 wherein said quaternary amine is acetyl choline chloride.

3. The method according to claim 1 wherein said tertiary amine is triethanolamine.

4. The method according to claim 1, wherein said primary amine is gamma-amino butyric acid.

5. The method according to claim 1, wherein said primary amine is ethyl 4-aminobutyrate.

6. The method according to claim 1, wherein said primary amine is tryptamine.

7. The method according to claim 1, wherein said amino acid is an amino acid from a hydrolized protein.

8. The method according to claim 1, wherein said primary amine is octopamine.

9. The method according to claim 1, wherein said composition further includes a bait toxin.

10. The method according to claim 9, wherein said bait toxin comprises suspension concentrates of oxymatrine and psoralen.

11. The method according to claim 9, wherein said bait toxin comprises an emulsion concentrate of Azadiractin.

12. A pest control composition attracting insects of the species *Ceratitis capitata* or of the species *Dacus cucurbitae* comprising N-acetyl thiazolidine carboxylic acid (NATC) and octopamine.

13. A pest control composition attracting insects of the species *Ceratitis capitata* or of the species *Dacus cucurbitae* comprising N-acetyl thiazolidine carboxylic acid (NATC) and at least one member selected from the group consisting of ammonium acetate: a quaternary amine; a tertiary amine; a primary amine; and an amino acid, wherein said composition further includes a bait toxin.

14. The composition according to claim 13, wherein said bait toxin comprises suspension concentrates of oxymatrine and psoralen.

15. The composition according to claim 13, wherein said bait toxin comprises an emulsion concentrate of Azadiractin.

16. An attractant for insects of the species *Ceratitis capitata* or of the species *Dacus cucurbitae* which comprise a trap or toxin for said insects and a composition comprising N-acetyl thiazolidine carboxylic acid (NATC).

17. The attractant according to claim 16 wherein said toxin comprises an emulsion concentrate of Azadiractin.

18. The attractant according to claims 16 wherein said toxin comprises suspension concentrates of oxymatrine and psoralen.

* * * * *